United States Patent [19]

Niemi

[11] Patent Number: 4,831,641
[45] Date of Patent: May 16, 1989

[54] METHOD AND APPARATUS FOR ANALYZING A VISIBLE OBJECT

[76] Inventor: Antti Niemi, Yrjö Liipolantie 5, 02700 Kauniainen, Finland

[21] Appl. No.: 883,853

[22] Filed: Jul. 10, 1986

Related U.S. Application Data

[63] Continuation of Ser. No. 130,919, Mar. 17, 1980, abandoned, which is a continuation of Ser. No. 760,892, Jan. 21, 1977, abandoned, which is a continuation of Ser. No. 525,126, Nov. 19, 1974, abandoned, which is a continuation-in-part of Ser. No. 352,573, Apr. 19, 1973.

[30] Foreign Application Priority Data

Apr. 24, 1972 [FI] Finland ................................ 1163/72

[51] Int. Cl.$^4$ ............................................. G06M 3/00
[52] U.S. Cl. ......................................... 377/53; 377/42; 382/6; 382/8; 250/564; 341/155
[58] Field of Search ...................... 235/92 PC, 92 DN; 340/146.3 F, 155; 356/102, 156; 358/294; 250/560, 223 R, 224, 359.1, 560–565, 571, 224; 377/11, 24, 53; 357/30; 209/524, 525, 536

[56] References Cited

U.S. PATENT DOCUMENTS

| | | | |
|---|---|---|---|
| 3,083,262 | 3/1963 | Hanlet | 340/173 LS X |
| 3,205,740 | 9/1965 | Groves et al. | 346/33 F X |
| 3,214,574 | 10/1965 | Landsman | 235/92 PC |
| 3,310,681 | 3/1967 | Hargens | 250/227 |
| 3,365,699 | 1/1968 | Foster | 209/525 X |
| 3,435,138 | 3/1969 | Borkan | 340/146.3 F X |
| 3,524,048 | 8/1970 | McMillin | 235/435 |
| 3,588,452 | 6/1971 | Kee | 340/146.3 F X |
| 3,588,480 | 6/1971 | Unger et al. | 250/224 X |
| 3,676,676 | 7/1972 | Somer | 250/207 X |
| 3,692,980 | 8/1972 | Getker et al. | 235/92 PC |
| 3,699,375 | 10/1972 | Weibel | 313/95 |
| 3,714,372 | 1/1973 | Rosen et al. | 235/92 PC |
| 3,729,619 | 4/1973 | Laycak | 377/53 X |
| 3,736,432 | 5/1973 | Sweet | 235/92 PC |
| 3,882,302 | 5/1975 | Deichmiller et al. | 235/92 DN |
| 3,983,364 | 9/1976 | Firehammer et al. | 235/440 X |

OTHER PUBLICATIONS

Millman et al, Pulse and Digital Circuits, McGraw-Hill Book Co., Inc., 1956, pp. 411–413.
Callahan, Optical Delay Line Compressor, IBM Technical Disclosure Bulletin, vol. 14, No. 8, 12/1977.
Hoeschele, Jr., Analog-To-Digital/-Digital-To-Analog Conversion Techniques, J. Wiley & Sons, Inc., 1968, pp. 360–363.
Schmid, Electronic Analog/Digital Conversions, Van Nostrand Reinhold Co., 1970, pp. 330–331.
Weckler, Fairchild Microwave and Optoelectronics, FPA600 Self Scanned Photodiode Array, Application Notes, 7/1970, pp. 1–9 and FIGS. 1–10.
Grob, Basic Television, McGraw-Hill Book Co., Inc., 1954, pp. 1–4.

Primary Examiner—William M. Shoop, Jr.
Assistant Examiner—Brian K. Young
Attorney, Agent, or Firm—Jordan and Hamburg

[57] ABSTRACT

The visually observable information is expressed in quantitive form according to an arrangement wherein there is firstly detected the distribution, size, shape and similar characteristics of objects appearing essentially in one level or plane of the sample and deviating visually from their environment. This detection is carried out by forming an image of the primary physical object on a light sensitive detector using known optic means, such as a microscope, in order to code the random information into a digital form, and thereupon the results of detection, that is the information thus brought into digital form, is transferred for further analysis to a computing and registering unit, such as a special purpose or process computer. Preferably, the detector unit comprises an array or matrix of light sensitive elements, such as photo-transistors.

9 Claims, 2 Drawing Sheets

METHOD AND APPARATUS FOR ANALYZING A VISIBLE OBJECT

This is a continuation application of Ser. No. 130,919 filed Mar. 17, 1980 (now abandoned), which is a continuation application to Ser. No. 760,892 filed Jan. 21, 1977 (now abandoned), which is a continuation application of Ser. No. 525,126 filed Nov. 19, 1974 (now abandoned), which is a continuation-in-part application of Ser. No. 352,573 filed Apr. 19, 1973 (now abandoned).

BACKGROUND OF THE INVENTION

1. Field of the Invention

The present invention relates to an improved method and apparatus for analyzing visible objects and for expressing visually observable information in a quantitative form, wherein the distribution, size, shape and similar characteristics related to the shape of objects appearing essentially on one level or plane of the sample and deviating from their environment both visually and to their other physical properties, are detected and the results of detection are immediately transferred to a computing unit for further treatment.

2. Description of the Prior Art

In industry, medicine, etc., it is often necessary to analyze materials or other objects which contain indefinitely distributed and situated points or areas of different intensities of greyness or color. Some examples of this are the analysis of a flowing suspension in the mineral refining industry and the analysis of a body fluid in medicine.

One previously known method of making such observations is to use an apparatus based on the principle of a normal TV camera; through, for example, a microscope or some other optics an appropriately enlarged or reduced image of the sample is reproduced on the detector surface. Such a system is, however, relatively expensive and complicated and therefore seldom practical. In addition, it must be noted that usually clear numerical data are necessary for the comparison and evaluation of different objects and for further processing of the information, and in that case a visual observation is not satisfactory.

Thus, the image information is converted into a pulse form even when using certain television systems, and in principle this takes place so, for example, that one or more threshold levels is selected for the signal which describes the brightness of the various points of the image, in which case a certain intensity range of the signal thus corresponds to a certain digital value, in other words, the light intensity signal is made discrete. The transformation of the image takes place with a continuous scanning signal, and the different statistical analyses for which these apparatuses are generally used, require for the computing a logic circuit system which is sometimes followed by a programmable computer. The transfer of information to the binary memory unit is possible only indirectly when a television system is used.

SUMMARY OF THE INVENTION

The objective of the present invention is to provide a method applicable to purposes referred to above and a recording and analyzing apparatus for carrying out the method, which apparatus has a relatively simple and thus also inexpensive structure and with which it is also simple to obtain digital data which can be directly stored in a binary memory and used for making an analysis by using, for example, a digital computer. The comparison, in a computer, of images or image series recorded in the memory from a dynamic process may further activate control and regulation measures automatically or these may be activated by the results of a statistical analysis of the compiled data.

In order to achieve the above objective the present invention provides a method of the character described, wherein the improvement comprises forming an image of the primary physical object or a part thereof on a light sensitive detector unit by using optics known as such, e.g. a microscope, in order to code the irregular, random information into a binary form; and transferring the information thus brought into a digital form for further analysis to a computing and registering unit, such as a process computer.

The invention thus provides a simple and reliable method for analysis that is applicable for many different purposes. The invention also provides a device for carrying out the above method, which comprises a detector unit including light sensitive electronic elements, appropriate optic means, such as a microscope for displaying the object on the detector unit in order to code the random information contained in the object into binary form, and finally a computing and registering unit for further processing of the digital-form information delivered by the detector.

Thus, the essential idea of the invention is that the detector used is a previously known electronic component unit, such as a linear photo diode array, photo-transistor matrix, or photo resistance matrix, which preferably also contains, in an integrated form, the necessary reading and switching means and which thus repeats, in a digital form, the image displayed on it. Alternatively, a similar detector which operates outside the wavelength range of visible light, such as an infrared sensitive detector, can also be used. The reading and switching means can also be separately constructed. It is also essential that the apparatus directly observes an object which contains physical particles, bodies or beings or which is composed of such, and it is not actually meant for processing information displayed in a drawn, written or photographic form.

An image of an illuminated or self-luminous object is obtained on this detector unit in a previously known manner with appropriate optics; a conventional microscope or some other optics can be used for the enlargement or reduction. Optical filters can be used to increase the contrast or to control the luminosity of the image. If, for example, a photo-diode array is used, the sample, the optics, or the array must naturally be moved in steps corresponding to the width of the array (for example, by using a step motor) during the formation of the image. The same naturally applies if the size of the digital unit is not otherwise sufficient to correspond to the size of the desired sample surface. The sample may also move by itself, for example, when running material flows by a measuring window, in which case the aforementioned controlled movement is not necessary.

In certain previously known methods and apparatuses a similar type of detector is used for reading punched cards, punched tape, or the like. Then the question is to bring into an electrically coded form previously visually coded digital data of which both the shape and possible locations are predetermined, while the present invention is actually meant to convert into a digital, electrically coded form, the shape or properties related to the shape of particles, bodies or beings which are visually observable, which are situated at random, and of which the physical shape is known or unknown.

DESCRIPTION OF THE PREFERRED EMBODIMENTS

The sample is displayed on the detector through a microscope, the detector consisting of, for example, a photo diode array. One detector suitable for this purpose is linear photo diode array FPA600 manufactured by SGS-Fairchild. It contains 48 photo diodes in an array and a dynamic shift register for reading the photo diodes.

The area of the image is divided into $m \times n$ ($n=48$) elements, and the state of luminosity of the elements is recorded as a binary number. The sample is moved along on a support with the help of a step motor, m steps per one image, in which case the degree of greyness of each image element is recorded.

The time period required for recording the image is mainly determined by the step motor, which must be quick and light. One practical motor is step motor 1D07 manufactured by Philips. The step motor is driven by a pulse series in a manner known as such.

A scanning reading circuit, which in this case is integrated in the same unit as the photo diodes, is naturally synchronized, by computer control, with the step motor which moves the sample. The video output of the integrated detector circuit is brought to a level which is suitable for, for example, TTL logic and is recorded in the transfer register, from where it is further transferred to the binary memory. This may be part of a special purpose computer which is permanently coupled to the apparatus and which can be either permanently programmed or freely programmable. A special purpose computer is advantageous for the reason that, for example, if a differentiation of only two degrees of greyness is desired, 1 bit is sufficient length for a data word. It can naturally be replaced by a standard type process computer.

Instead of a photo diode array of the aforementioned type the used detector can also be, for example, a matrix which contains all $m \times n$ elements. Such matrixes are now available in a prefabricated form (for example, the TIL137 manufactured by Texas Instruments Inc.) or can be constructed by using discrete components. One component suitable for the latter purpose is photo transistor LS600 manufactured by Texas Instruments Inc. Then preferably one light sensitive component corresponds to one image element.

The recording of the information takes place, for example, one array at a time, but in comparison with the previous case, the step motor and the movement of the sample can be eliminated. If the light intensity of the sample is high, the photo-transistors can be coupled directly to the TTL logic for recording the image information; discriminators which can be controlled in a known manner or discriminators with predetermined steps are used for discriminating smaller intensities of light (about 0.05-20 $mW/cm^2$).

Figure 1:
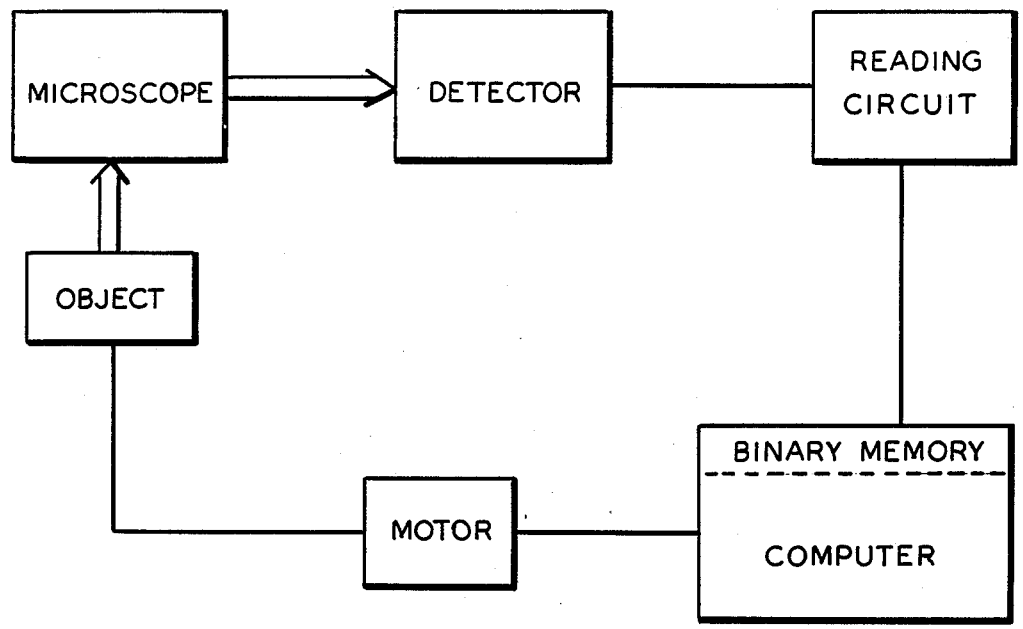
FIG. 1 is a schematic block diagram of an analyzing system according to the present invetion.
Figure 2:
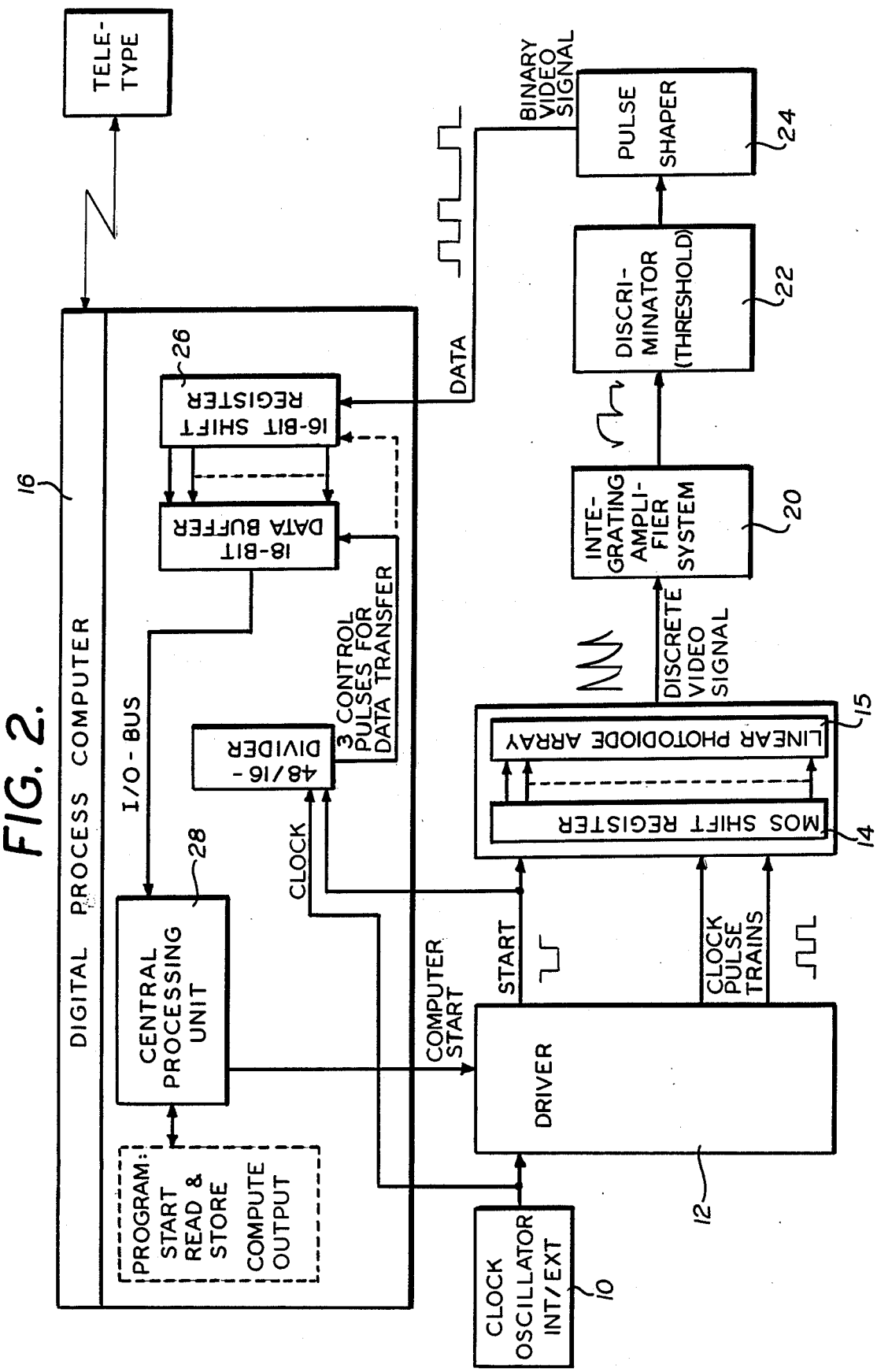
FIG. 2 is a schematic block diagram of the analyzing system according to the present invention but which illustrates the switching and reading means in greater detail.

Turning now to FIG. 2 which illustrates the switching and reading means in greater detail, there is shown a detector 15 which, by way of example may be a FPA-600 manufactured by SGS-Fairchild, containing 48 photo diodes as a linear array and connected intimately to a shift register 14. An oscillator 10 produces a continuous clock pulse train, which is directed by a driver 12 both as such and as another inverted clock pulse train to the shift register 14. Reading of the state of the photo diodes in the photo diode array 15 is not initiated until a start pulse is provided from the computer 16. After the start signal is provided each photo diode of the photo diode array 15 is accessed in sequence with the successive clock pulses. A pulse train is produced with each pulse having an amplitude which is proportional to the degree of illumination of the corresponding photo diode element, with a frequency determined by the clock oscillator 10. The pulse train is preferably transferred first into an integrating amplifier 20. A discriminator 22 connected to the amplifier involves an adjustable threshold by which means the pulses corresponding to the light and dark parts of the physical object being observed are separated. A pulse shaping circuit 24 transforms the output of the discriminator 22 into the final binary pulse train which is transferred into the digital computer 16.

If the word length of the computer 16 is smaller than 48 bits, it is practical to read the signal in sequences of 16 bits, for example in a 16-bit shift register 26 as shown in FIG. 2. Transfer of data into a central processing unit 28 of the computer 16 takes place when the 16-bit shift register 26 of the computer 16 is full.

A new reading and switching operation may be started at once or after a desired interval of time after the completion of the preceding operation has elapsed. The moment of the new start is normally determined by the computer program.

The heretofore described reading and switching means 20, 22, 24 which controls the reading from the photo diode array 15 and connects it to the computer 16 may form an integrated unit together with the photo diode array 15 or they may be separately constructed as shown in FIG. 2.

It must be noted in general that any appropriate, previously known solutions and circuits can be used for detecting the state of the light sensitive elements of the detector and for transferring and recording the information. For this part the apparatus according to the invention contains electronic logic circuits and their interface devices which are well known as such to those skilled in the art.

For example the digital computer with a binary memory is a well known item, and the same applies to the standard process computers previously mentioned and which regularly are able to perform the necessary input and output data processing operations. It is also evident that special purpose computers with corresponding abilities can be constructed for specific aims like that described hereinbefore. The reading circuit block covers the reading and switching means outside the detector and required for reading of the detector unit and for production of the final digital input. Of these means, the functions, combinations and constructional examples of the required driver and clock oscillator circuits and of the amplifier, particularly of one used as a reset integrator, for signal extraction are presented in the Fairchild Application Notes "Fairchild Microwave and Optoelectronics FPA600 Self Scanned Photodiode Array", by F. P. Weckler, July 10, 1970.

As regards the application of applicant's invention to the analysis of processes which are inherently dynamic, examples of such applications are the analysis of a flowing suspension in the mineral refining industry, the analysis of a body fluid in medicine, analyzing running material flowing by a measuring window, identification of solid particles in a flowing process fluid, observation of the degree of fill of a silo for ore, and analysis of partially white rocks on a conveyor belt for their lime content.

According to applicant's invention the object field under observation may be compared with a reference pattern stored in the computer memory through a reference observation and storing of the field of view may be effected under some standard conditions. The observations and comparisons are made and the deviations from the reference pattern computed repeatedly, and if a sufficient deviation or a combination of deviations is once found, required measures can be taken. Also now the dynamics of the object are essential, though usually only rarely do they lead to reactions. This kind of function is needed e.g. with regard to the guarding of a hopper disposed to blocking and subsequent brimming, and in connection to the guarding or monitoring of a door, room or other space where no admittance is allowed.

A method for automatic supervision of such processes where a visually observable progress is normally present, may be effected according to the present invention. Observed patterns of the dynamic process can be regularly compared with individual images of a series of reference images stored in digital form in the computer from a sequential reference observation of the standard process cycle and if sufficient deviations are noted, the required measures can be taken. An example is the control of the assembly of mechanical parts on an automatic assembly line or in an automatic machine.

Dynamic processes, such as the types described above often require, in addition to the observation and analysis, also control, and a method of automatic control for which the processing of visual information is necessary. After the observed patterns of the dynamic process have been compared with a reference pattern, or after they have been analyzed statistically, suitable control or regulation measures which are known to those skilled in the art can be activated. Suitable examples are the automatic control of the fill of a silo for ore, and mechanical separation of rocks with a high lime content from other rocks on, or at the end of a conveyor belt, whereby the individual control operations may be located partly inside and partly exterior to the computer.

It is thought that the invention and many of its attendant advantages will be understood from the foregoing description and that it will be apparent that various changes may be made in the form, construction, and arrangements of the parts without departing from the spirit and scope of the invention of sacrificing all of its material advantages. The form heretofore described being merely a preferred embodiment thereof.

What is claimed is:

1. An improved method for analyzing a material containing visible objects of the type wherein a continuous two-dimensional real image of said objects or a part thereof is formed by focusing optical means, and serial, digital video signals corresponding to said image are transferred to a computing and registering unit, wherein the improvement comprises, in combination:
    transforming the optically formed image into discrete electric signals by means of a detector unit located in the plane of the continuous two-dimensional image and consisting of at least one row of individually responsive detector elements;
    reading serially periodically said discrete electric signals and obtaining separate electric output signals, corresponding serially to each detector element;
    coding said output signals into said serial, digital video signals; and
    extracting by means of a freely programmable digital real-time computer, used as the computing and registering unit, quantities representing the size, boundaries and characteristics related to the shape of said visible objects contained in a flowing material of which no physical sample is detached for the analysis, and expressing said quantities in quantitative digital form.

2. A method according to claim 1 wherein said flowing material comprises solid articles on a continuously operating conveyor.

3. An improved device for analyzing a material containing visible objects of the type wherein a continuous two-dimensional real image of said objects or a part thereof is formed by focusing optical means; and serial, digital video signals corresponding to said image are transferred to a computing and registering unit, wherein the improvement comprises, in combination:
    a detector unit consisting of at least one row of individually responsive detector elements located in the plane of said continuous two-dimensional image and transforming the optically formed image into discrete electric signals;
    means for periodically transforming said discrete electric signals with separate electric output signals being obtained corresponding serially to each detector element, and for coding said output signals into said serial, digital video signals; and
    the computing and registering unit being a freely programmable digital real-time computer programmed to extract quantities representing the size, boundaries and characteristics related to the shape of said visible objects contained in a flowing material of which no physical sample is detached for the analysis, and to express said quantities in quantitative digital form.

4. An improved method for analyzing a flowing material containing visible objects, of the type wherein light transmitted onto the surface of a detector unit is transformed into locally discrete electric signals by said detector unit consisting of a row of individually responsive detector elements, and wherein digital signals are transferred to a digital computing unit capable of storing variable reference models and making comparisons with them, wherein the improvement comprises, in combination:
    forming with focusing optical means, located between the material and the detector unit, a continuous two-dimensional continuously variable real image of said objects on the surface of the detector unit, said image being formed as the flowing material passes a fixed area,
    reading serially, periodically, under control of said computer, said locally discrete electric signals with separate electric output signals being obtained corresponding serially to each detector element, thresholding by means of at least one adjustable threshold, said output signals into the form of a serial, digital video signal to be transferred to said computing unit, and extracting by means of a freely programmable digital real-time computer, used as the computing unit, quantities representing the size, boundaries and characteristics related to /the shape of said visible objects, and expressing said quantities in quantitative digital form.

5. An improved device for analyzing a flowing material containing visible objects, of the type wherein light transmitted onto the surface of a detector unit consisting of a row of individually responsive detector elements is transformed into locally discrete electric signals by said detector unit; and wherein is used a digital computing unit receiving said discrete electric signals and capable of storing variable reference models and making comparisons with them, wherein the improvement comprises, in combination:

focusing optical means located between said material and said detector unit and forming a continuous two-dimensional continuously variable real image of said objects on the surface of the detector unit, said continuously variable image being formed as the flowing material passes a fixed area;

means for reading serially, periodically, under control of said computing unit, said locally discrete electric signals with separate electric output signals being obtained corresponding serially to each detector element, and for thresholding, by means of at least one adjustable threshold, said output signals into the form of a serial, digital video signal to be transferred to said computing unit; and the digital computing unit being a freely programmable digital real-time computer programmed to extract quantities representing the size, boundaries and characteristics related to the shape of said visible objects, and to express said quantities in quantitative digital form.

6. An improved method for analysing a flowing material of the type wherein light transmitted from the material onto the surface of a detector unit through lenses located between said flowing material and said detector unit is transformed into locally discrete electric signals by said detector unit consisting of a row of individually responsive detector elements, and wherein serial digital signals are obtained and handled further, wherein the improvement comprises, in combination:

applying a visual observation to primary physical visible bodies transported by said flowing material, by focusing with said lenses a continuous two-demensional continuously variable real image of said flowing material, containing said bodies, on the surface of said detector unit, said image being formed as said flowing material passes a fixed area, reading serially, under computer control, periodically said locally discrete electric signals with separate electric output signals being obtained corresponding serially to each detector element, thresholding by means of at least one adjustable threshold said output signals into the form of a serial, digital video signal, transferring the obtained serial digital video signals to freely programmable digital real-time computer, and extracting by means of said computer quantities representing the size, boundaries and characteristics related to the shape of said visible bodies, and expressing said quantities in quantitative digital form.

7. An improved method for visual analysis, of the type whrein light transmitted from a moving material containing primary physical visible bodies onto the surface of a detector unit, through lenses located between said material and said detector unit, is transformed into locally discrete electric signals by said detector unit consisting of a row of individually responsive detector elements which signals are read, thresholded by at least one adjustable threshold, and handled further, wherein the improvement comprises, in combination:

applying a visual observation to said bodies contained in a moving material, by forming with said lenses a continuous two-demensional continuously variable real image of said bodies in said material on the surface of said detector unit, said image being formed as the material passes a fixed area, reading serially, periodically, under computer control, said locally discrete electric signals with separate electric output signals being obtained corresponding serially to each detector element and submitting said output signals to said thresholding, transferring said signals, thresholded into the form of a serial, digital video signal, to a freely programmable digital real-time computer, and extracting by means of said computer quantities representing the size, boundaries and characteristics related to the shape of said visible bodies, and expressing said quantities in quantitative digital form.

8. An improved device for analysing a flowing material of the type including a detector unit consisting of a row of individually responsive detector elements, lenses located between said material and said detector unit, said lenses transmitting light from the material onto the surface of the detector unit and the light being transformed by the detector unit into locally discrete electric signals, whereby serial digital signals are obtained and handled further, wherein the improvement comprises in combination:

the lenses being adapted to focus a continuous two-dimensional continuously variable real image of primary physical visible bodies transported by said flowing material, on the surface of said detector unit, said image being formed as said flowing material passes a fixed area, means for reading serially, under computer control, periodically said locally discrete electric signals with separate electric output signals being obtained corresponding serially to each detector element, means for thresholding, by using at least one adjustable threshold said output signals into the form of a serial, digital video signal, a freely programmable digital real-time computer adopted to receive said digital video signal, and the computer being programmed to extract quantities representing the size, boundaries and characteristics related to the shape of said visible bodies, and to express said quantities in quantitative digital form.

9. An improved device for visual analysis of a moving material containing primary physical visible bodies, including a detector unit consisting of a row of individually responsive detector elements, lenses located between said material and said detector unit for transmitting light from said material onto the surface of a detector unit, which transforms the light into locally discrete electric signals, said signals being read, thresholded by at least one adjustable threshold, and handled further, wherein the improvement comprises, in combination:

the lenses being adapted to form a continuous two-dimensional continuously variable real image of said bodies in said material on the surface of said detector unit, said image being formed as the material passes a fixed area, means for reading serially, periodically, under computer control, said locally discrete electric signals with separate electric output signals being obtained corresponding serially to each detector element, and to submit said output signals to said thresholding, and a freely programmable digital real-time computer adopted to receive said signals, thresholded into the form of a serial, digital video signal, and to extract quantities representing the size, boundaries and characteristics related to the shape of said visible bodies, and to express said quantities in quantitative digital form.

* * * * *

UNITED STATES PATENT AND TRADEMARK OFFICE
CERTIFICATE OF CORRECTION

PATENT NO. : 4,831,641
DATED : May 16, 1989
INVENTOR(S) : Antti Niemi

It is certified that error appears in the above-identified patent and that said Letters Patent is hereby corrected as shown below:

Column 6,
Lines 17, 46 and 47, delete ", boundaries and characteristics related to the shape"
Lines 57-59, delete "capable of storing variable reference models and making comparisons with them"

Column 7,
Lines 9 and 10, delete ", boundaries and characteristics related to the shape"
Line 18, delete "is used";
Line 19, change "receiving" to -- receives --;
Lines 20 and 21, delete "and capable of storing variable reference models and making comparisons with them";
Lines 39 and 40, delete ", boundaries and characteristics related to the shape"

Column 8,
Lines 2, 3, 31-32, 60 and 61, delete ", boundaries and characteristics related to the shape"

Column 10,
Lines 8 and 9, delete ", boundaries and characteristics related to the shape"

Signed and Sealed this

Twenty-eighth Day of September, 2004

JON W. DUDAS
*Director of the United States Patent and Trademark Office*